US010258396B2

(12) United States Patent
Kazanovicz et al.

(10) Patent No.: US 10,258,396 B2
(45) Date of Patent: Apr. 16, 2019

(54) TPLO BONE PLATE

(71) Applicant: MWI Veterinary Supply Co., Boise, ID (US)

(72) Inventors: Andrew J. Kazanovicz, Holland, MA (US); David J. Anderson, III, South Glastonbury, CT (US)

(73) Assignee: MWI Veterinary Supply Co., Boise, ID (US)

( * ) Notice: Subject to any disclaimer, the term of this patent is extended or adjusted under 35 U.S.C. 154(b) by 150 days.

(21) Appl. No.: 15/133,434

(22) Filed: Apr. 20, 2016

(65) Prior Publication Data

US 2016/0310184 A1      Oct. 27, 2016

Related U.S. Application Data

(60) Provisional application No. 62/150,524, filed on Apr. 21, 2015.

(51) Int. Cl.
*A61B 17/80*    (2006.01)
*A61B 17/17*    (2006.01)

(52) U.S. Cl.
CPC ...... *A61B 17/8061* (2013.01); *A61B 17/1728* (2013.01); *A61B 17/1739* (2013.01); *A61B 17/8052* (2013.01)

(58) Field of Classification Search
CPC .................. A61B 17/8061; A61B 17/8095
See application file for complete search history.

(56) References Cited

U.S. PATENT DOCUMENTS

| 5,304,180 | A | * | 4/1994 | Slocum | A61B 17/8014 |
| | | | | | 606/282 |
| 5,709,686 | A | | 1/1998 | Talos et al. | |
| 6,096,040 | A | * | 8/2000 | Esser | A61B 17/8061 |
| | | | | | 606/280 |
| 6,623,486 | B1 | | 9/2003 | Weaver et al. | |
| 6,669,701 | B2 | | 12/2003 | Steiner et al. | |
| D536,453 | S | | 2/2007 | Young et al. | |

(Continued)

FOREIGN PATENT DOCUMENTS

CN        203954787 U      11/2014

OTHER PUBLICATIONS

Written Opinion of the International Searching Authority dated Jul. 28, 2016 for International Application No. PCT/US2016/028343, eight (8) pages, unnumbered.

(Continued)

*Primary Examiner* — David W Bates
(74) *Attorney, Agent, or Firm* — Iandiorio Teska & Coleman, LLP

(57) ABSTRACT

A bone plate is dimensioned for securing the rotated cut segment of an upper tibia to the lower portion of the tibia as part of a tibial leveling osteotomy procedure for an animal. The bone plate includes an elongated shaft, a head portion pre-bent with respect to the elongated shaft, and a transition between the elongated shaft and head portion including opposing concave sidewalls. The elongated shaft has a centerline and the pre-bent head portion has a centerline angled with respect to the centerline of the elongated shaft to dispose the elongated shaft collinear or approximately collinear with respect to the lower portion of the tibia and to better fit the head portion to the rotated cut segment of the upper tibia.

26 Claims, 14 Drawing Sheets

(56) References Cited

U.S. PATENT DOCUMENTS

| | | | |
|---|---|---|---|
| 7,740,648 B2 | 6/2010 | Young et al. | |
| 7,771,457 B2* | 8/2010 | Kay | A61B 17/8061 606/280 |
| 8,177,818 B2 | 5/2012 | Wotton, III | |
| 8,506,607 B2 | 8/2013 | Eckhof et al. | |
| 8,523,921 B2* | 9/2013 | Horan | A61B 17/8061 606/281 |
| 2002/0156474 A1 | 10/2002 | Wack et al. | |
| 2004/0260294 A1 | 12/2004 | Orbay et al. | |
| 2005/0240187 A1* | 10/2005 | Huebner | A61B 17/80 606/71 |
| 2006/0004362 A1* | 1/2006 | Patterson | A61B 17/8057 606/291 |
| 2006/0149275 A1 | 7/2006 | Cadmus | |
| 2007/0233106 A1* | 10/2007 | Horan | A61B 17/8061 606/282 |
| 2008/0300637 A1 | 12/2008 | Austin et al. | |
| 2009/0018588 A1* | 1/2009 | Eckhof | A61B 17/8057 606/280 |
| 2010/0030276 A1 | 2/2010 | Huebner et al. | |
| 2010/0057133 A1* | 3/2010 | Simon | A61B 17/8061 606/280 |
| 2011/0264149 A1* | 10/2011 | Pappalardo | A61B 17/8019 606/286 |
| 2011/0301655 A1 | 12/2011 | Price et al. | |
| 2012/0078252 A1 | 3/2012 | Huebner et al. | |
| 2014/0336712 A1 | 11/2014 | Strnad et al. | |
| 2015/0127011 A1* | 5/2015 | Dunlop | A61B 17/80 606/88 |
| 2015/0374420 A1* | 12/2015 | Hashmi | A61B 17/8061 606/281 |
| 2016/0128745 A1* | 5/2016 | Sidebotham | A61B 17/8014 606/281 |

OTHER PUBLICATIONS

Kowaleski, et al., "The Effect of Tibial Plateau Leveling Osteotomy Position on Cranial Tibial Subluxation: An In Vitro Study", Veterinary Surgery, 34:332-336, 2005.

* cited by examiner

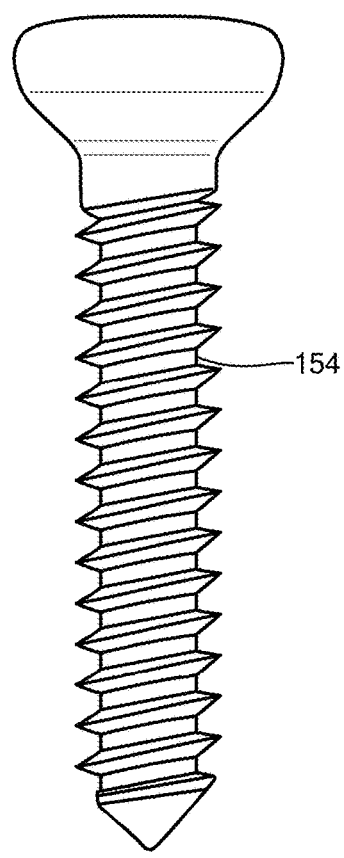
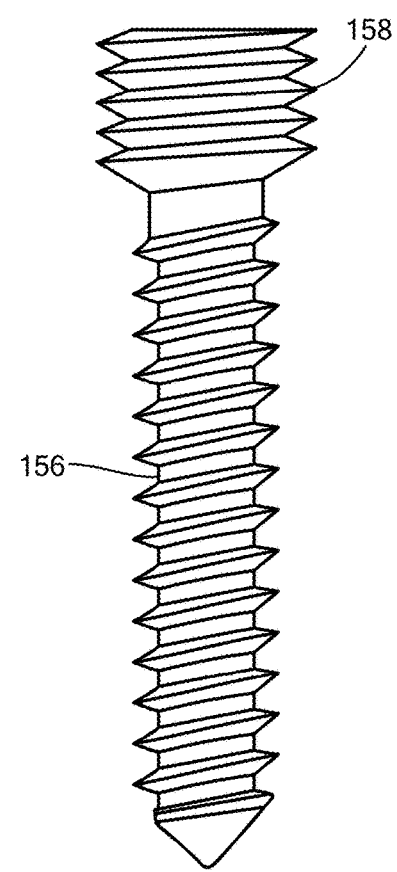
FIG. 11      FIG. 12

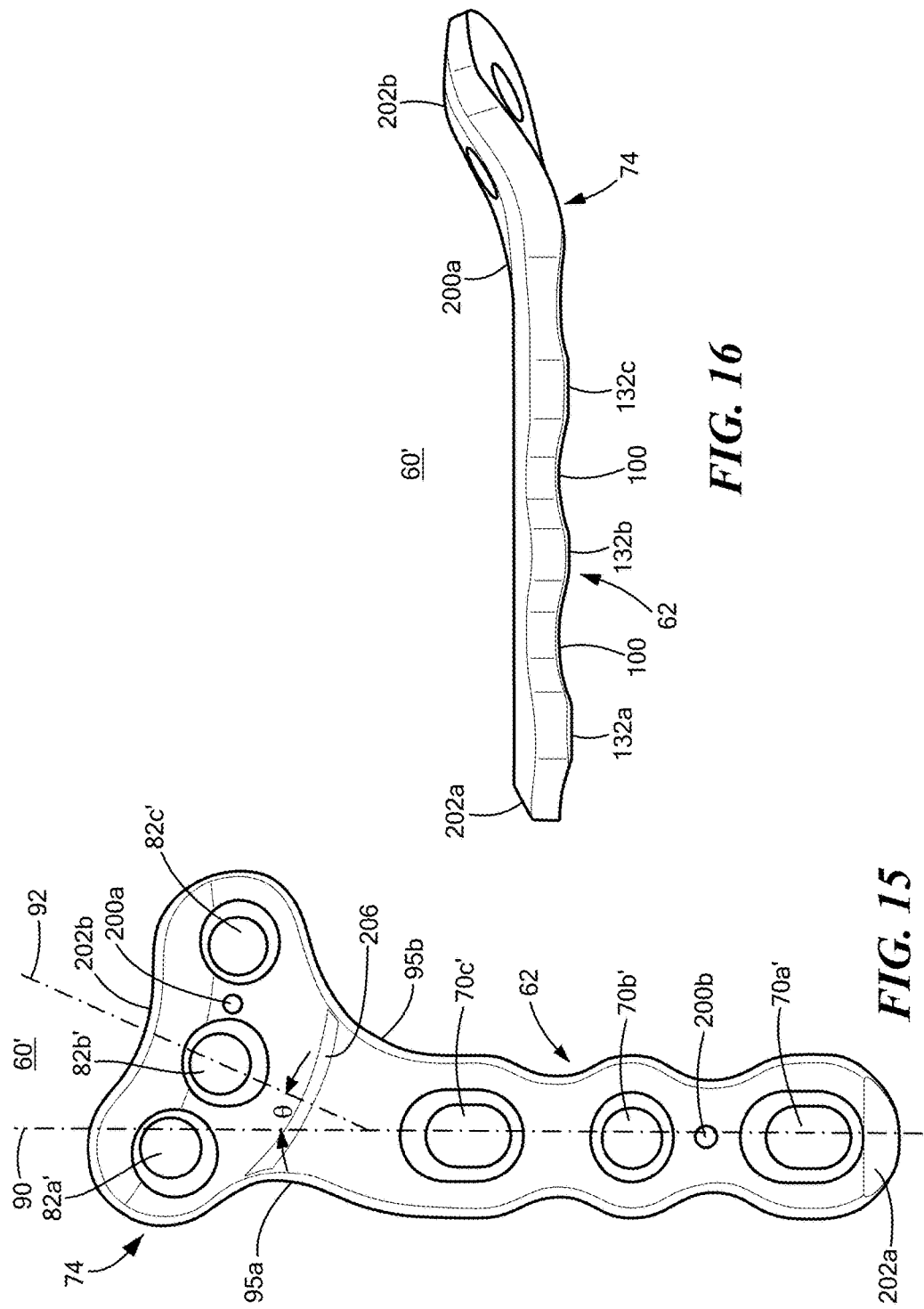

US 10,258,396 B2

TPLO BONE PLATE

RELATED APPLICATIONS

This application claims benefit of and priority to U.S. Provisional Application Ser. No. 62/150,524 filed Apr. 21, 2015, under 35 U.S.C. §§ 119, 120, 363, 365, and 37 C.F.R. § 1.55 and § 1.78, which is incorporated herein by this reference.

FIELD OF THE INVENTION

This invention primarily relates to a bone plate dimension for securing the rotated cut segment of an upper tibia to the lower portion of the tibia as part of a tibial leveling osteotomy procedure for an animal.

BACKGROUND OF THE INVENTION

The purpose of the tibial plateau leveling osteotomy (TPLO) procedure is to stabilize the cranial cruciate ligament (CCL)—deficient canine stifle by reducing the tibial plateau slope thereby neutralizing the cranial tibial thrust force or redirecting it into a caudal direction. See, for example, Kowaleski, et al. "The Effect of Tibial Plateau Leveling Osteotomy Position on Cranial Tibial Subluxation: An In Vitro Study, Veterinary Surgery, 34:332-336 (2005), incorporated herein by this reference. A segment of the upper tibia is cut and rotated and then rejoined to the lower portion of the tibia using a bone plate. See, for example, U.S. Pat. No. 8,523,921 incorporated herein by this reference.

Most bone plates are designed for specific procedures and/or bones. There are numerous examples. See, for example, U.S. Pat. No. 6,096,040 (designed for the proximal humerus). There are also numerous patents for various bone plate screw hole designs and other aspects of bone plates.

Further, there are several bone plate designs specifically for use in TPLO procedures. See, for example, U.S. Pat. Nos. 5,304,180; 7,740,648 (and D536,453); U.S. Pat. No. 8,177,818 (by the assignee hereof); U.S. Pat. No. 8,523,921; and U.S. Patent Application Publication No. 2006/0149275 all incorporated herein by this reference.

In some TPLO procedures, the cut is made fairly high on the upper tibia with reported benefits as opposed to the case where a large portion of the upper tibia is cut and rotated. During some TPLO procedures, including when the cut is made higher and due to the rotated tibia segment, some prior TPLO plates require that the lower leg section of the plate be angled with respect to the lower tibia. Sometimes, the head section of the TPLO plate is not tailored or optimized for the now smaller rotated cut upper tibia segment. The result could be a TPLO procedure where the TPLO plate has to be bent and/or shaped for each animal. The surgery time is thus increased when inter-operative bending of the TPLO plate is required. The result can also be bone plates which do not properly secure the two tibia sections together, bone screws which do not properly hold (shorter bone screws may have to be used) and/or which extend into the stifle (knee) joint causing damage to the articular and periarticular surfaces possibly leading to osteoarthritis. Other TPLO plates have a head shape which interfere with features of the cut, rotated tibial plateau.

SUMMARY OF THE INVENTION

In aspects of some examples of the invention, a new TPLO plate is provided which is better tailored to the TPLO procedure especially when the cut is made fairly high on the upper tibia. The lower leg section or elongated shaft remains aligned or mostly aligned with respect to the lower tibia and yet the head portion conforms to the cut rotated upper tibial portion. Inter-operative bending of the TPLO plate may be minimized. One result is a shortening of the surgical procedure and less metal fatigue. The two tibial sections are properly secured together and the bone screws used properly hold the bone plate in place after the operation. The bone screws are prevented from extending into the stifle. It is preferred that the new TPLO plate is anatomically pre-contoured so the elongated shaft portion is aligned with the long axis of the tibia to allow for more bone purchase by screws (e.g., longer screws can be used) and greater stiffness while at the same time providing a better fit of the head portion to the rotated portion of the tibia.

Featured is a bone plate dimensioned for securing the rotated cut segment of an upper tibia to the lower portion of the tibia as part of a tibial leveling osteotomy procedure for an animal. The preferred bone plate includes an elongated shaft with a top surface and bottom bone contacting surface between opposing sides of the bone plate elongated shaft. Screw holes in the elongated shaft extend from the top surface to the bottom bone contacting surface for securing the elongated shaft to the lower portion of the tibia. A head portion is pre-bent with respect to the elongated shaft and with a top surface and a bottom bone contacting surface between sidewalls of the bone plate head portion. Screw holes in the head portion extend from the top surface to the bottom bone contacting surface thereof for securing the head portion to the rotated cut segment of the upper tibia. There is a transition between the elongated shaft and head portion including opposing concave sidewalls. The elongated shaft has a centerline and the pre-bent head portion has a centerline angled with respect to the centerline of the elongated shaft in order to dispose the elongated shaft collinear or approximately collinear with respect to the lower portion of the tibia and to better fit the head portion to the rotated cut segment of the upper tibia.

In some examples, the angle between the centerline of the elongated shaft and the centerline of the head portion is 15°-40°, preferably 25°-30°. Preferably, the angle between the centerline of the elongated shaft and the centerline of the head portion is smaller for larger size bone plates and larger for smaller size bone plates.

Different size bone plates may have a head portion with a cloverleaf shape and other size bone plates have a head portion with a crescent shape. Preferably, the leg portion lies in a first plane and the head portion is bent upwardly and lies in the second plane angled with respect to the first plane. The bone plate head portion may have a bottom bone contacting surface which is anatomically contoured to match the contour of the rotated cut tibia segment.

Preferably, the elongated shaft opposing sides have spaced curved notches for further bending the head portion relative to the elongated shaft to vary the angle between the centerline of the head portion and the centerline of the elongated shaft during a TPLO procedure. Spaced curved notches are typically disposed between adjacent screw holes in the elongated shaft. Also, the elongated shaft bottom bone contacting surface may include spaced transverse grooves to reduce contact between the elongated shaft bottom surface and the lower portion of the tibia. The bone plate screw holes in the elongated shaft and/or head portion may include a central opening, a plurality of bores spaced around said central opening and intersection surfaces formed from a common intersection of the central opening and adjacent bores. Screw holes may further include a countersink above said intersection surfaces for a non-locking screw.

The bone plate may be made of a titanium alloy. The bone plate may also include one or more k-wire holes. The shaft may have a beveled distal end. The head portion may have a beveled proximal end. The bone plate may further include a contoured registration mark on the top surface of the plate proximate the transition to assist a surgeon in placing the bone plate on the rotated cut segment of the upper tibia. The bone plate may further include a drill guide plate configured the same as the bone plate and including top surface drill guide ports oriented to overlie the screw holes in the bone plate.

Also featured is a set of different size bone plates dimensioned for securing the rotated cut segment of an upper tibia to the lower portion of the tibia as part of a tibial leveling osteotomy procedure for an animal.

In each plate, there is a transition between the elongated shaft and head portion including opposing concave sidewalls. The elongated shaft has a centerline and the head portion has a centerline angled with respect to the centerline of the elongated shaft to dispose the elongated shaft collinear or approximately collinear with respect to the lower portion of the tibia and to fit the head portion to the rotated cut segment of the upper tibia. The angle between the centerline of the elongated shaft and the centerline of the head portion is different for different size bone plates in the set.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIGS. 11 and 12 show two different types of bone screws useful in connection with the bone plate screw holes shown in FIGS. 9-10;

FIGS. 15-16 are views of another TPLO bone plate in accordance with an example of the invention.

DETAILED DESCRIPTION OF THE INVENTION

Figure 3:
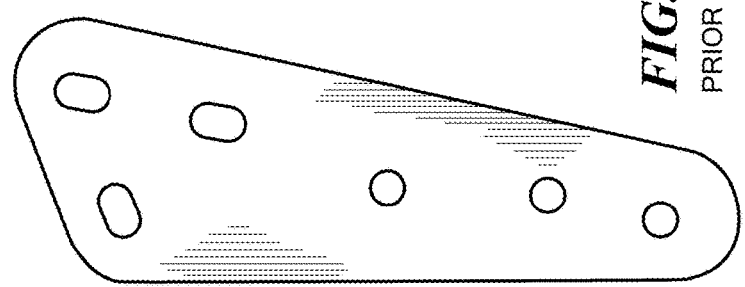
FIG. 3 is a schematic front view showing an example of a prior art TPLO bone plate in accordance with U.S. Pat. No. 8,177,818.
Figure 2:
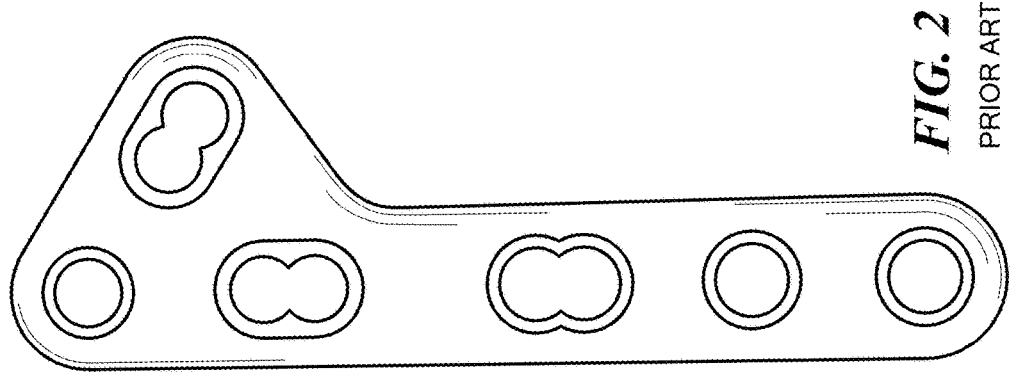
FIG. 2 is a schematic front view showing an example of a prior art TPLO bone plate in accordance with U.S. Pat. No. 7,740,648.
Figure 1:
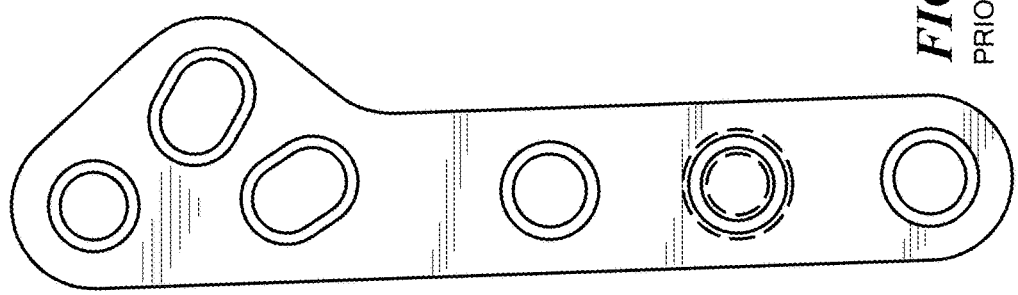
FIG. 1 is a schematic front view showing an example of a prior art TPLO bone plate in accordance with U.S. Pat. No. 5,304,180.
Figure 4:
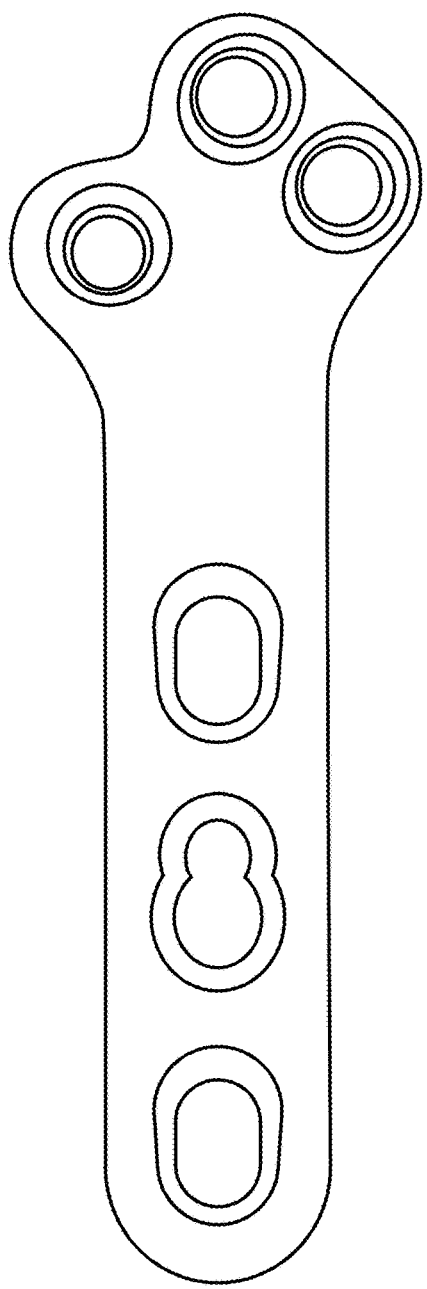
FIG. 4 is a schematic front view showing an example of a prior art TPLO bone plate in accordance with U.S. Pat. No. 8,523,921.
Figure 5:
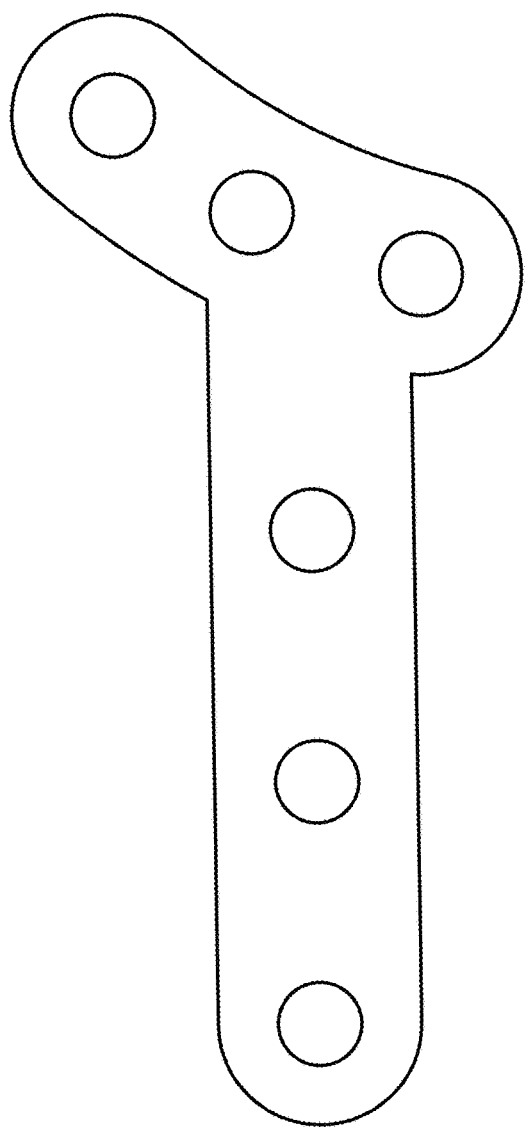
FIG. 5 is front view showing an example of a prior art bone plate in accordance with U.S. Publication No. 2006/0149275.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIGS. 1-5 show various prior art TPLO bone plates which may not be optimized or specifically tailored for a TPLO procedure where the cut is made fairly high on the upper tibia. Some prior TPLO bone plates may require that the lower leg section or shaft portion be angled with respect to the lower tibia. In some prior art TPLO plates, the bone plate head section is not optimized or tailored for the now smaller rotated cut upper tibia segment. Other possible limitations associated with some prior TPLO plates are discussed above with respect to the Background section hereof.

Figure 14:
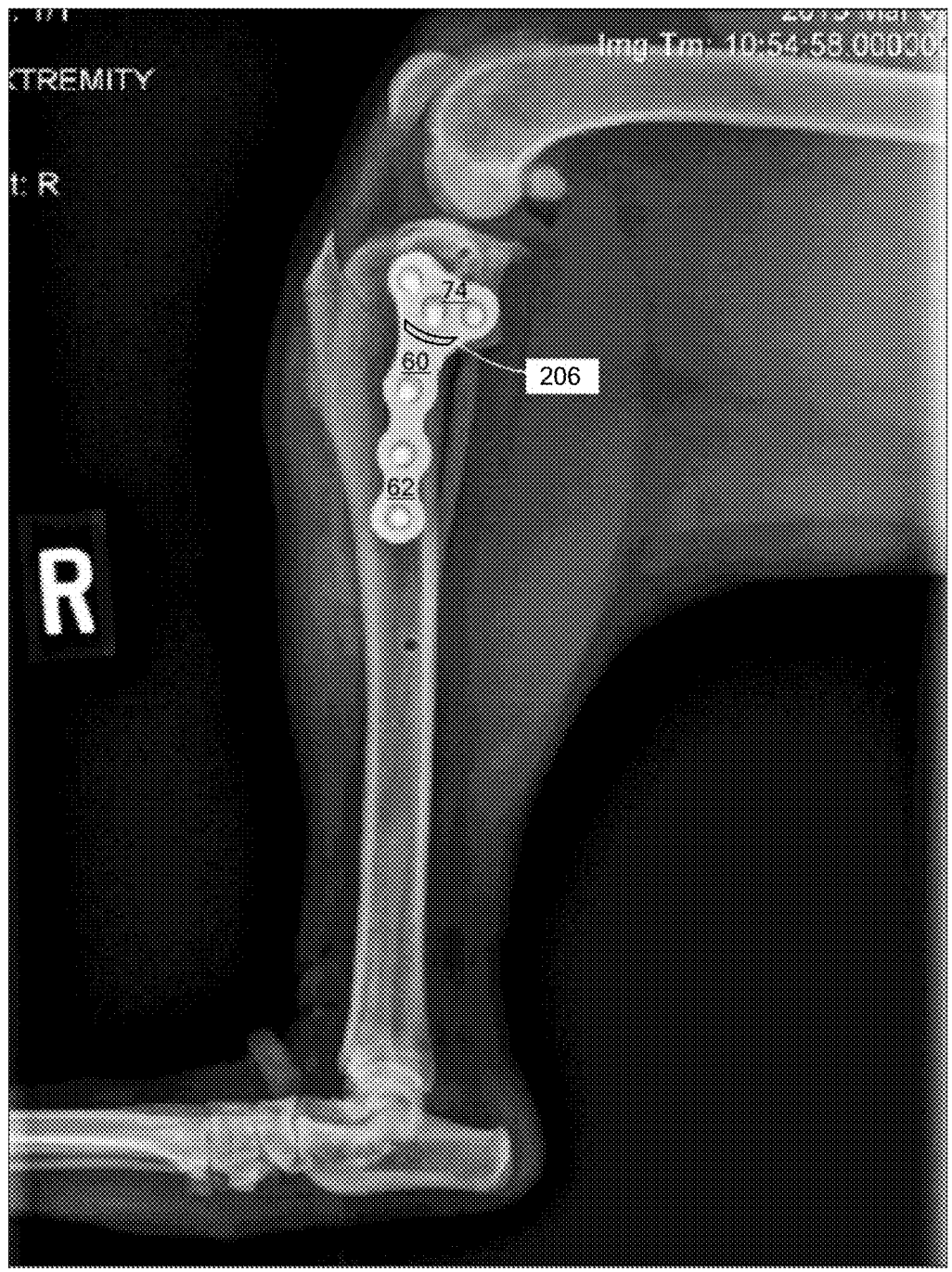
FIG. 14 is a schematic view showing the bone plate place securing the upper cut rotated tibial portion to the lower tibial portion.

FIG. 6A-6D show an example of a new TPLO bone plate 60 with elongated shaft or leg 62 having top surface 64, bottom surface 66, and opposing side surfaces 68a and 68b. Shaft 62 in this particular example includes three screw holes 70a, 70b, and 70c for securing shaft 62 to the lower portion of the tibia as shown in FIG. 14.

Head portion 74 extends from shaft 62 as shown and has a top surface 76 and bottom surface 78 between opposing sides 80a and 80b. Screw holes 82a, 82b, and 82c in head portion 74 are designed to secure head portion 74 to the rotated cut segment of the upper tibia and the leg portion or shaft is secured to the lower portion of the tibia.

Figures 6A, 6B:
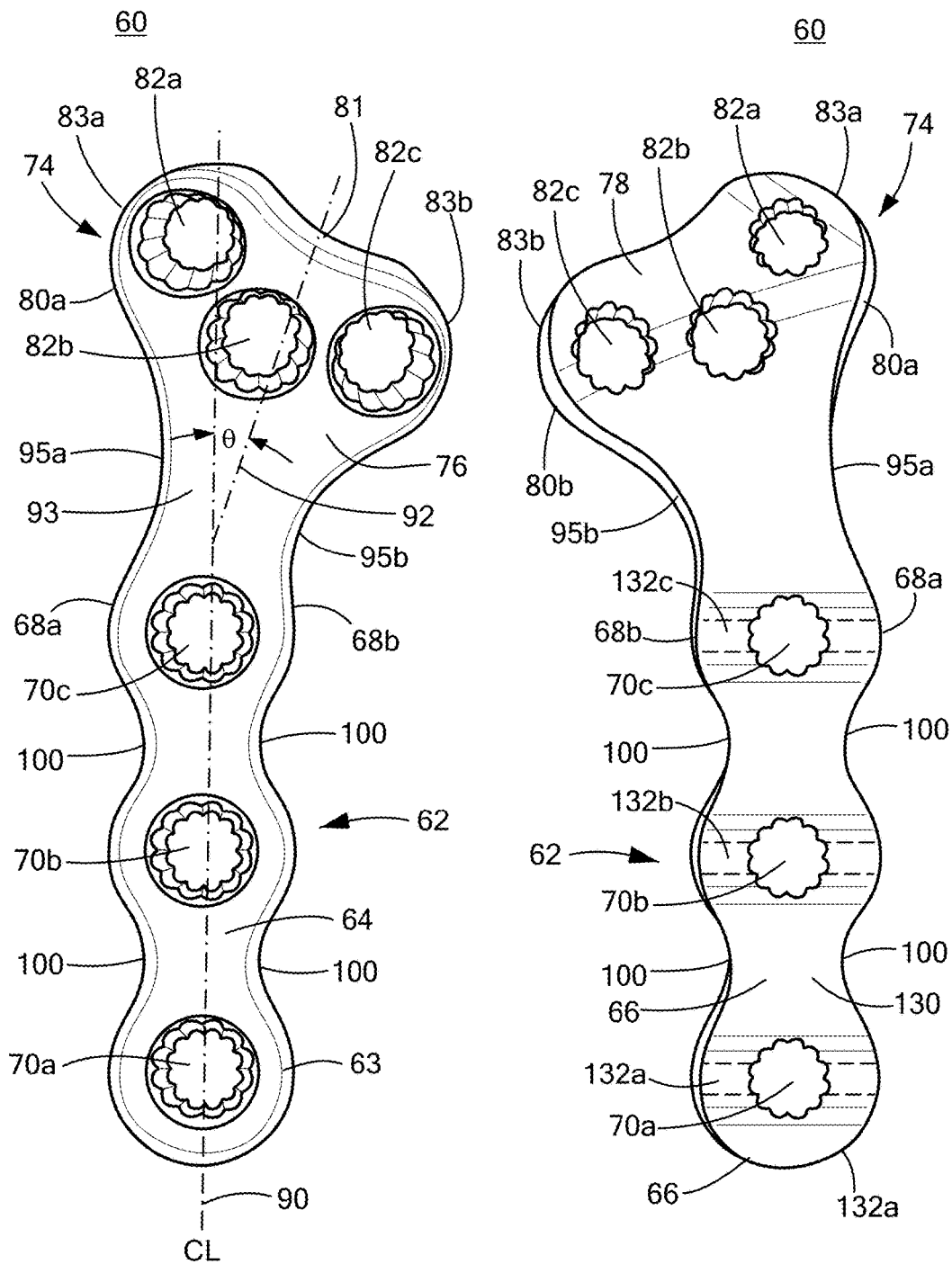
FIG. 6A is a schematic top view showing one preferred TPLO bone plate in accordance with examples of the invention.
FIG. 6B is a schematic bottom view of the bone plate shown in FIG. 6A.

As shown in FIG. 6A, at the transition 93 between elongated shaft 62 and head portion 74 there are opposing concave sidewalls 95a and 95b between the top of shaft 62 and the bottom of outer lobes 83a and 83b of head portion 74. Both transition sidewalls are angled in the same direction (to the right of FIG. 6A) with respect to the centerline 90 of shaft 62. This pre-bend of the head portion optimizes placement of the head portion on the cut upper tibia. After the reduced width transition section due to concave sidewalls 95a and 95b, the bent head portion generally flairs to a wider top end shown in FIG. 6 as a crescent style head. A cloverleaf head design is also possible, see FIG. 7 and head portion 74'. Another head style bone plate is shown in FIG. 8.

Note that the head portion 74, FIG. 6 is thus angled with respect to the shaft (to the right or left depending on the leg undergoing a TPLO procedure). This pre-bend in the XY plane of the TPLO plate (the plane of the drawings sheet of FIG. 6A) helps align the elongated shaft portion 62 collinear with the lower tibia especially when the cut is made fairly high on the upper tibia. When the elongated shaft portion is aligned with or closely aligned with the long axis of the tibia, longer bone screws can be used and/or there is better contact between the elongated shaft portion and the lower portion of the tibia for greater strength, holding power, and stiffness provided by the bone plate. The bend in the XY plane of the TPLO plate also optimizes placement of the head portion 74 on the cut rotated upper tibia segment for easier and more effective attachment thereto. As shown, shaft 62 has a centerline 90 in this particular example, head portion 74 has centerline 92 and there is angle θ between shaft centerline 90 and head portion centerline 92. θ may range from 15°-40°, preferably from 25° to 30° and may be different depending on the size of the bone plate. Head 74 may also be shaped differently depending on the size of the bone plate. FIG. 6 shows a crescent style head but other head shapes such as cloverleaf shapes may be used. In general, a crescent style has outer lobes 83a and 83b around the outer holes 80a and 80b with a dip 81 between the two outer lobes at the centerline 92 of head portion 74. A cloverleaf design, FIG. 7 has another lobe 83b between the two outer lobes 83a, 83c generally located at the head portion centerline.

Preferably, the bend angle θ is smaller for larger size bone plates and larger for smaller size bone plates. The bone plate of FIG. 6 may be a 3.5 mm standard bone plate configured for a smaller radial osteotomy blade (e.g., 21-24 mm radius). θ was 25°. The 3.5 mm broad bone plate shown in FIG. 7 was specifically designed for a larger radial osteotomy blade (27-30 mm) and θ was 25°. Note now head portion 74 is a cloverleaf style head with three lobes 83a, 83b, and 83c and four screw holes 82a, 82b, 82c, and 82d. FIG. 8 shows a 2.7 mm stand and crescent head plate with only two screw holes and a configuration which is specifically designed for a 15-18 mm radial osteotomy blade. θ was 28°.

In one example, these plates are sold as a set. Table 1 includes several types of plates available in the set.

TABLE 1

| Size | θ | Blade Size | Head Style | Length | Head Width |
|---|---|---|---|---|---|
| 3.5 mm broad | 25° | 27-30 mm | Cloverleaf (four holes) | 82 mm | 27 mm |
| 3.5 mm standard | 25° | 21-24 | Crescent (three holes) | 59 | 24 |
| 2.7 mm broad | 28° | 18-21 | Cloverleaf (three holes) or crescent (three holes) | 56 | 19 |
| 2.7 mm standard | 28° | 15-18 | crescent (three holes) or crescent (two holes) | 43 | 18 |
| 2.4 | 30° | 12-15 | Crescent (two holes) | 34 | 13 |
| 2.0 | 30° | 9-12 | Crescent (two holes) | 28 | 11 |

Figure 6C:
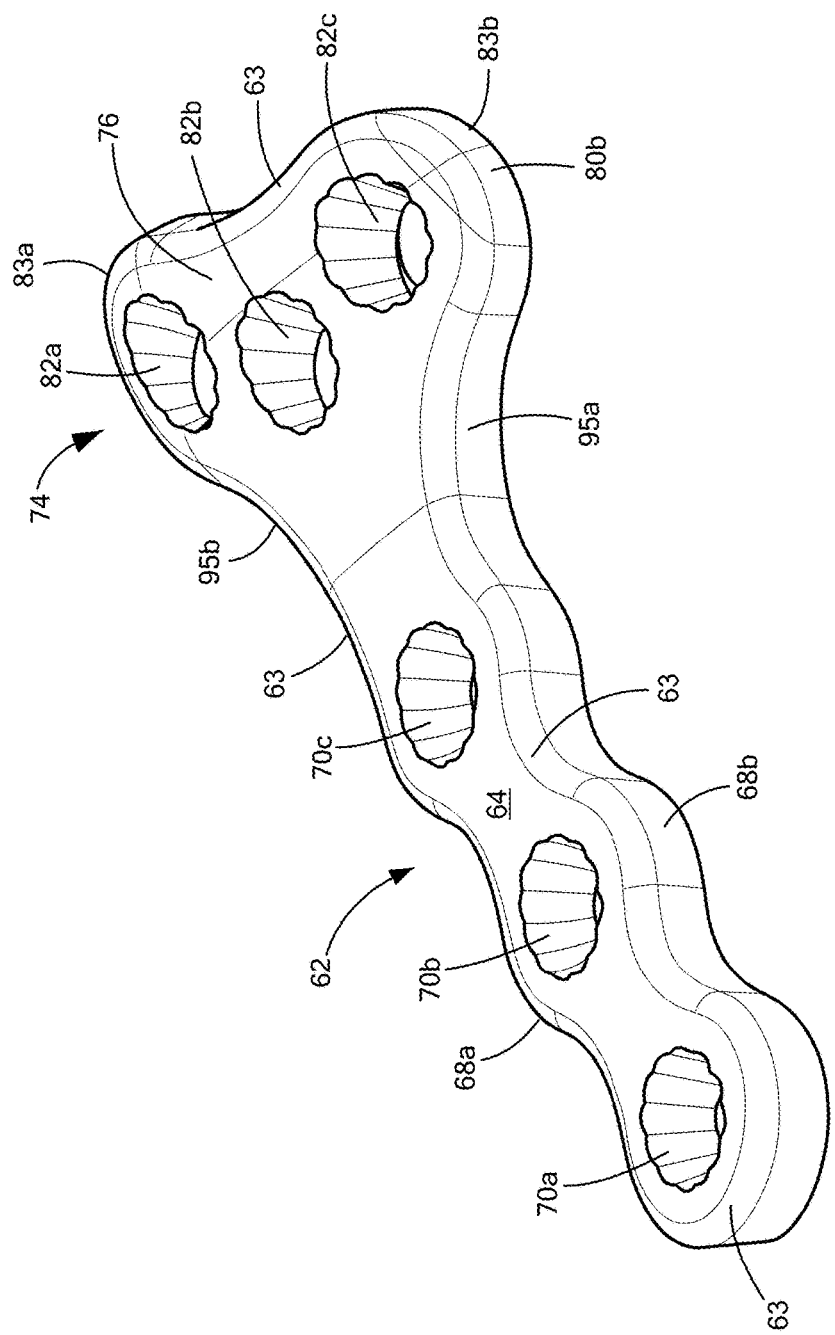
FIGS. 6C-6I are additional views of a 3.5 mm right side bone plate.
Figures 7, 8:
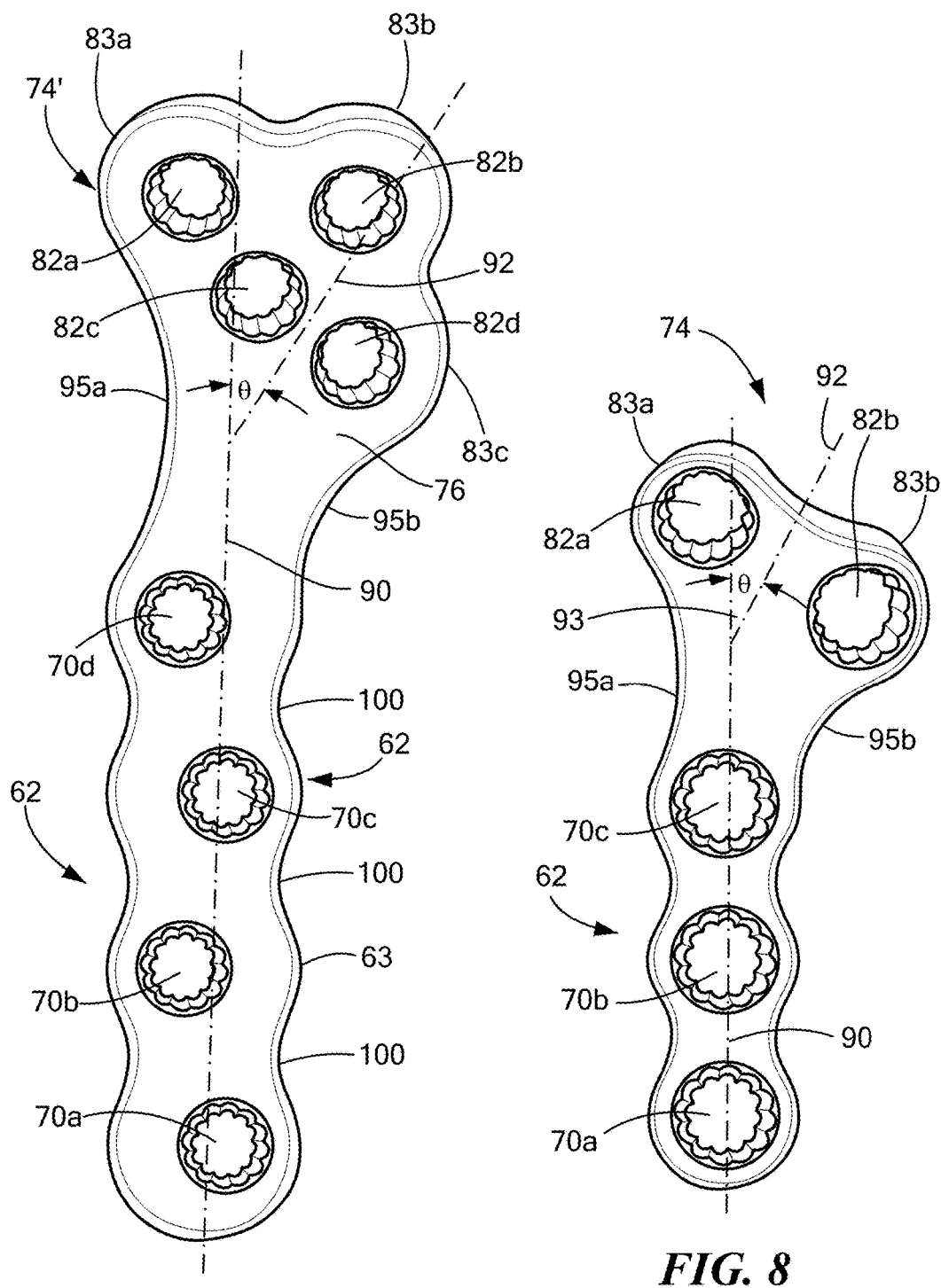
FIG. 7 is a schematic front view showing another example of a TPLO bone plate in accordance with embodiments of the invention.
FIG. 8 is a schematic front view showing still another example of TPLO bone plate in accordance with embodiments of the invention.

FIG. 6C shows how the top side entire periphery of the bone plate may have a beveled radius at 63 to eliminate sharp edges to provide less stress to skin or tissue.

Figure 6D:
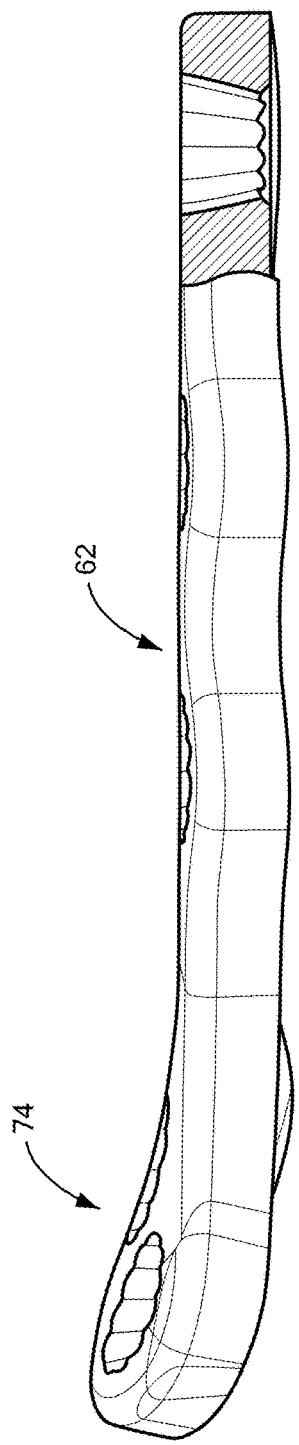
Figure 6E:
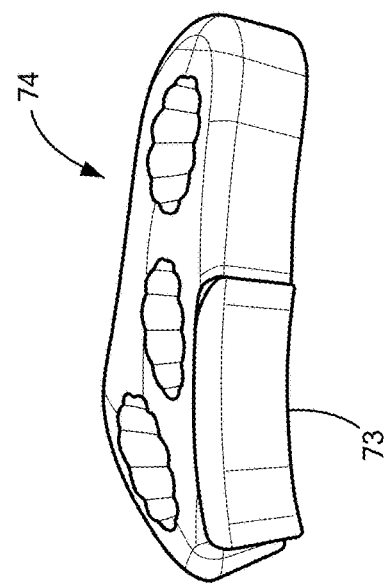
Figure 6F:
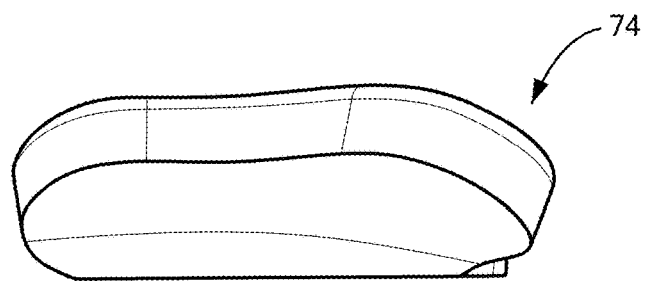
Figure 6G:
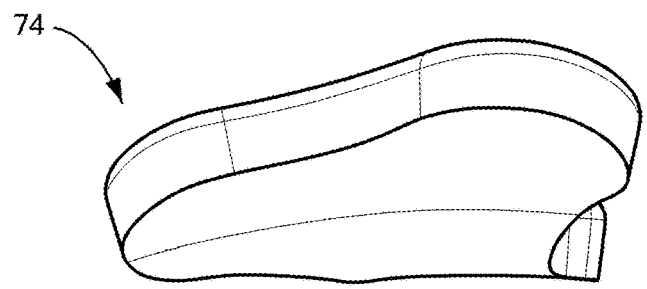
Figure 6H:
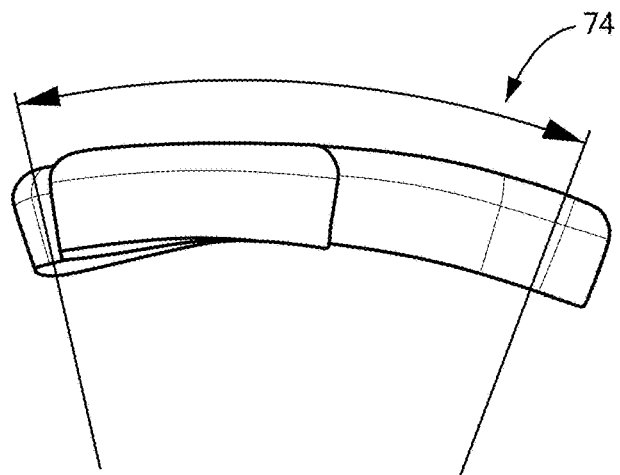
Figure 6I:
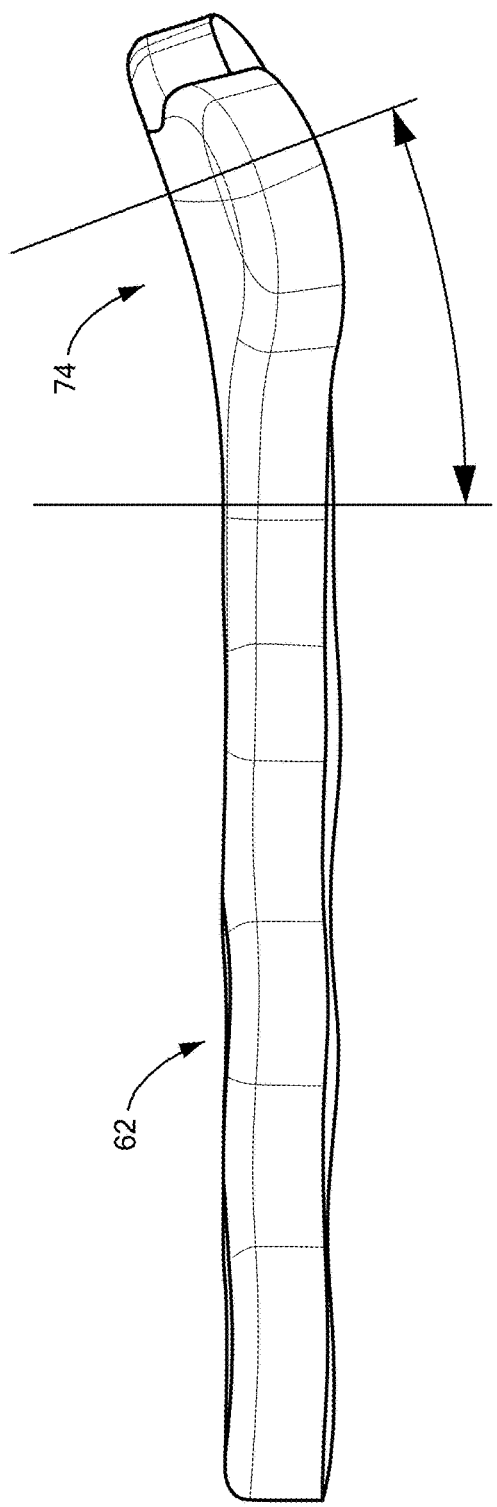

In FIG. 6D it can also be seen that head portion 74 is also preferably bent upwardly and lies in a different plane than shaft portion 62. Preferably head portion 74 is bent both upwardly, twisted, and bent to the right or left depending on whether the leg undergoing the TPLO procedure is a right leg or a left leg. The upward bend angle may be 24° and the head portion 74, FIG. 6E bottom surface may be anatomically contoured as shown at 73 to match the contour of a typical rotated cut tibial segment. FIG. 6F shows a twist bend (e.g., 27°) of the nose of the head end of the plate. FIG. 6G shows the head 74 before the twist bend is made. The preferred order of contouring is (1) the bottom surface contour bend, (2) the upward head bend, and (3) the upward head twist. The underside contour 73, FIG. 6H bends the entire underside of the plate down at an angle of approximately 45°. The proximal contour bends the proximal region of the plate up at angle of approximately 20° as shown in FIG. 6I.

The bottom surface contour bend may be a bend at a 30 mm radius along the centerline of the plate over a 45° sector. The upward bend of the head with respect to the plane of the leg may be 24° and also the head may be bent at an angle with respect to the centerline plane of the plate (e.g., 70.5° with respect to the centerline axis shown in FIG. 6A). The clockwise twist of the head is with respect to the plane of the upward bend of the head. The plate may be physically bent or it may be machined to include these preferred bends.

FIG. 6A also shows how elongated shaft 62 has opposing sides 68a and 68b with spaced curved notches 100 between adjacent screw holes 70a and 70b and then again between screw holes 70b and 70c. These notches reduce the width of the shaft between the screw holes (e.g., by between 25-39% depending on the size of the plate). In this way, the angle θ can be adjusted if needed using a bending tool. These notches also reduce the contact between the shaft bottom surface and the tibia to promote healing.

FIG. 6B in particular also shows how the bottom of the TPLO plate preferably includes spaced transverse grooves 130 between the screw holes 70a and 70b and between screw holes 70b and 70c machined across the width of the reduced width span between opposing side notches. This leaves the bottom bone contacting surfaces small (e.g., 11 mm wide by 6 mm long for a 3.5 mm plate). See strips 132a, 132b, and 132c extending across the bottom of the bone plate from one side to the other interrupted by a shaft screw hole. The narrow bone contacting strips or lands 132a, 132b, and 132c are shown in FIG. 6B when there are three screw holes 70a, 70b, and 70c. The result is a reduction in contact between the shaft bottom surface and the tibia to promote healing. That is, the bone plate only contacts the bone at strips or lands 132.

Figure 9:
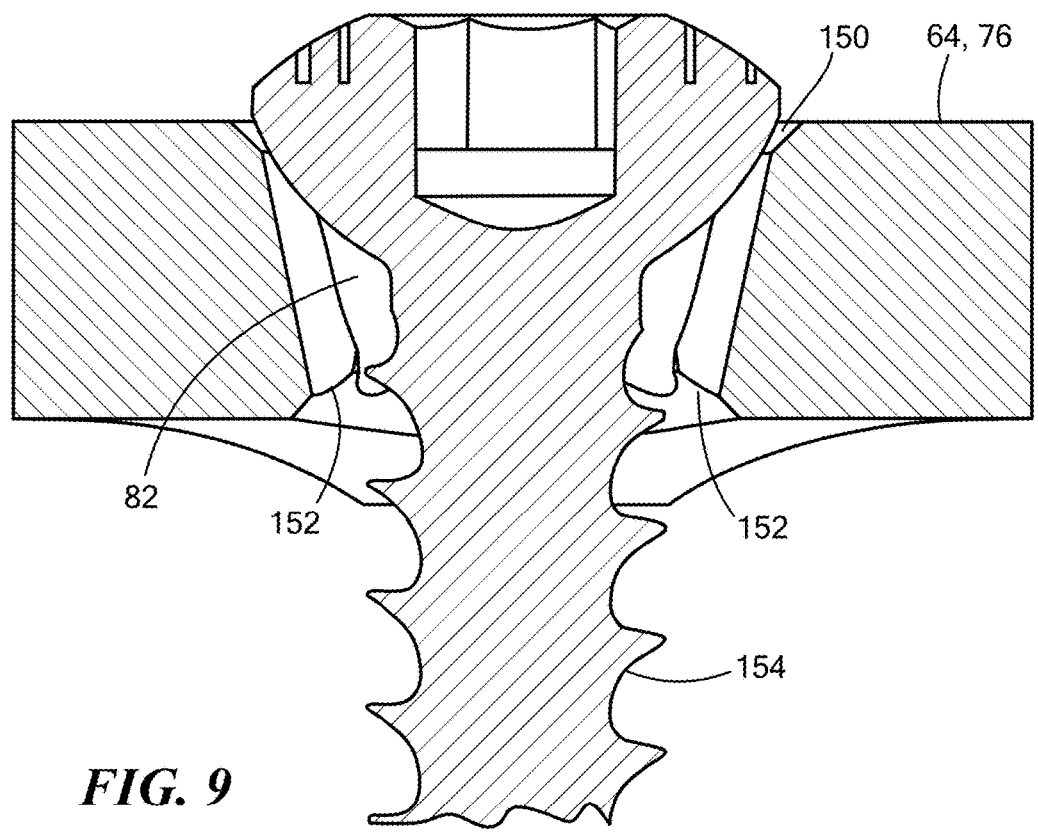
FIGS. 9-10 are schematic views showing an example of a novel screw hole for the bone plates.
Figure 10:
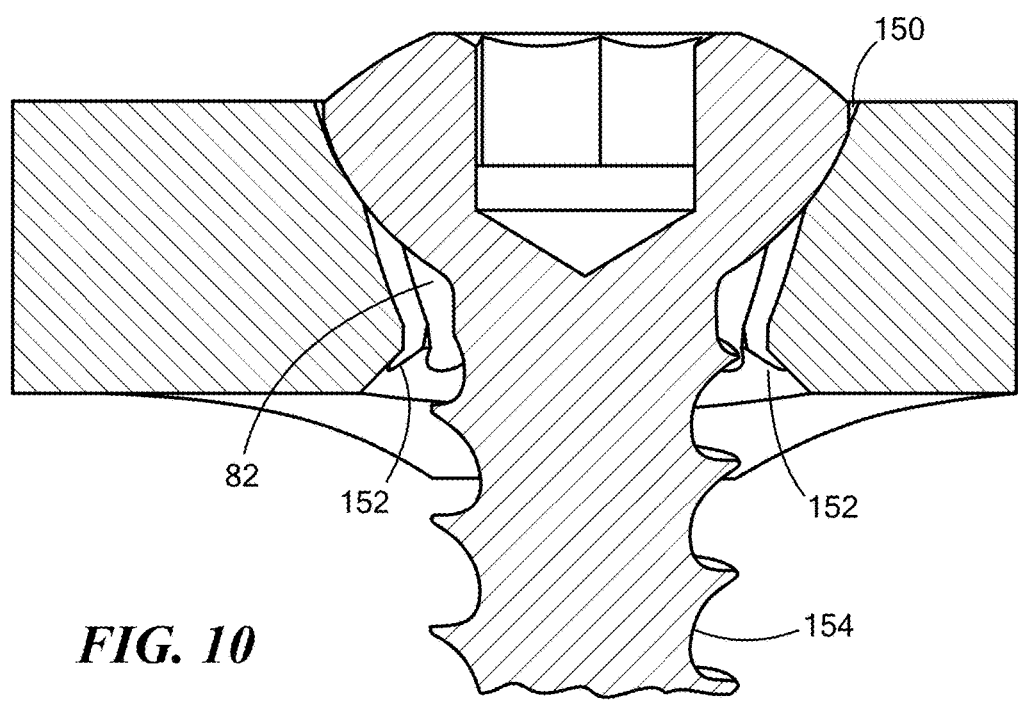

The screw holes in the shaft and head portion may include in a central opening, a plurality of bores spaced around the central opening, and intersection surfaces formed from a common intersection of the central opening and the adjacent bores as shown in the figures. See, U.S. Pat. No. 8,506,607 incorporated herein by this reference. Other types of screw holes may be used including locking, non-locking, combination locking and non-locking, or combinations of the same. See U.S. Pat. Nos. 6,623,486; 5,709,686; and 6,669,701 incorporated herein by this reference. In one example shown in FIGS. 9-10, the locking screw hole includes a countersink 150 above the intersection surfaces 152 for non-locking screw 154, FIG. 11. Locking screw 156, FIG. 12 may also be used with threads 158 on the head thereof configured to engage the intersection surfaces of the locking screw holes configured as set forth in U.S. Pat. No. 8,506,607.

Preferably, the bone plates are made of a titanium alloy such as Ti Grade 2, Grade 4, or Ti6Al4V for enhanced biocompatibility. Stainless steel (316LVM) may also be used. A matte/satin finish may be provided to prevent glare of the plate during surgery.

Figure 13:
FIG. 13 shows a prior bones plate used in TPLO procedures.

FIG. 13 shows how a prior TPLO bone plate (FIG. 4) failed to properly fit the anatomy causing the distal part of the plate to kick forward resulting in suboptimal placement of the distal screws (too cranial or too caudal). FIG. 14 shows the proper fit provided by the TPLO bone plate of the invention.

In FIGS. 15 and 16, plate 60' has non-locking holes 82a', 82b' and 82c' in head portion 74 and non-locking dynamic compression holes 70a' and 70a' in shaft 62. Proximal 200a and distal 200b k-wire holes may be provided for temporary fixation to prevent the plate from shifting during locking screw insertion. Leg distal 202a and head proximal 202b beveled ends may be provided to facilitate tunneling of the bone plate under soft tissues in a minimally invasive manner. A registration mark such as a laser etched line 206 is preferably provided at the junction between head portion 74 and shaft portion 62 on the top surface of the plate to assist the surgeon in correctly placing the plate. The contour of line 206 matches and is placed over the cut of the upper tibia. See FIG. 14.

Figure 17:
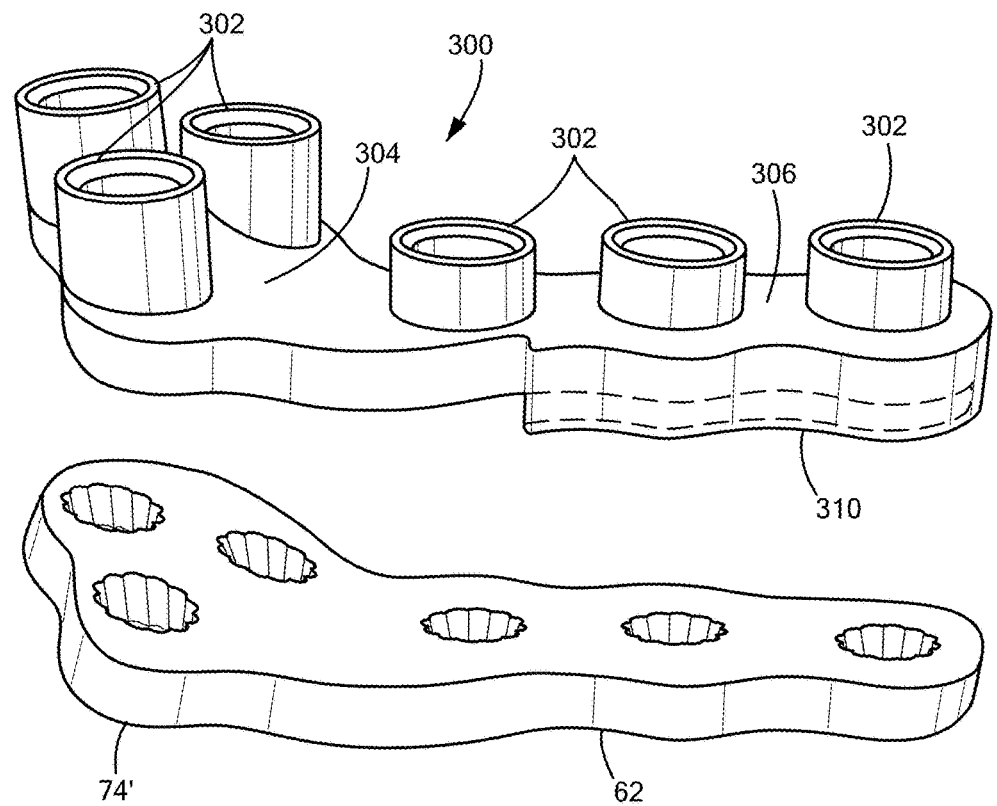
FIGS. 17-18 are views of an example of a snap on drill guide plate.
Figure 18:
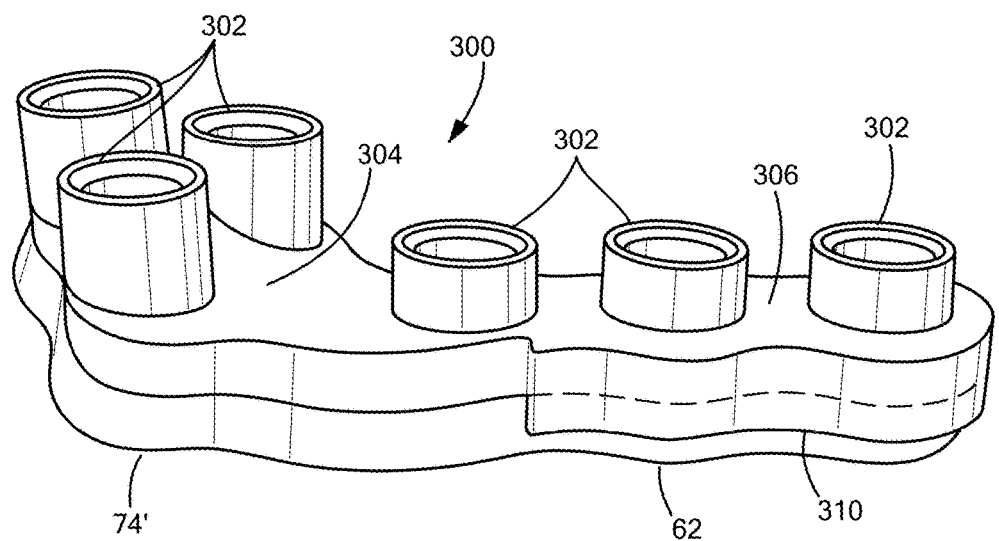

FIGS. 17-18 show snap on drill guide plate 300 here configured to match the contours of a cloverleaf style head bone plate (see FIG. 7). Similar snap on drill guide plates will match the size and contours of all the bone plates styles and sizes. Thus, a given drill guide plate will include a bone plate matching head 304 and leg section 306 each with drill guide ports (e.g., raised cylinders) 302 oriented to overlie the bone plate screw holes. Each port will receive a standard drill guide (typically a tube with a pilot hole for the drill bit) in order to ensure a given bone screw does not, for example, proceed into the knee joint. Thus, the drill guide ports are correctly oriented to optimally insert a given bone screw at the correct angle.

To retain the guide plate in place on the bone plate during drilling operations, a snap fit between the guide plate and the bone plate is preferred. In one example, the leg section 306 includes depending periphery sidewall 310 contoured to fit over the periphery of the bone plate leg section side surfaces. Other snap fit means may be used to releasably retain the drill guide plate on the bone plate during drilling operations.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A bone plate dimensioned for securing a rotated cut segment of an upper tibia to a lower portion of the tibia as part of a tibial leveling osteotomy procedure for an animal, the bone plate comprising:
   an elongated shaft with a top surface and bottom bone contacting shaft surface between opposing sides of the bone plate elongated shaft;
   shaft screw holes in the elongated shaft extending from the top surface to the bottom bone contacting shaft surface for securing the elongated shaft to the lower portion of the tibia;
   a head portion bent with respect to the elongated shaft and with a top surface and a bottom bone contacting head portion surface between sidewalls of the bone plate head portion;
   head portion screw holes in the head portion extending from the top surface to the bottom bone contacting head portion surface thereof for securing the head portion to the rotated cut segment of the upper tibia;
   a transition between the elongated shaft and head portion including opposing concave sidewalls, the elongated shaft having a centerline located centrally between the opposing sides of the shaft and the bent head portion having a centerline located centrally between opposing sidewalls of the head portion and angled with respect to the centerline of the elongated shaft at an angle of 25°-30° to dispose the elongated shaft collinear or approximately collinear with respect to the lower portion of the tibia and to fit the head portion to the rotated cut segment of the upper tibia;
   the head portion having a crescent shape and including two outer head portion screw holes, a first outer lobe about one outer head portion screw hole and a second outer lobe about the other outer head portion screw hole, a dip between the two outer lobes at the centerline of head portion, and a third head portion screw hole between the two outer head portion screw holes;
   the centerline of the shaft bisecting all the shaft screw holes; and
   the centerline of the head portion intersecting the third head portion screw hole.

2. The bone plate of claim 1 in which the shaft portion lies in a first plane and the head portion is bent upwardly and lies in a second plane angled with respect to the first plane and the head portion has a twist bend.

3. The bone plate of claim 2 which the head portion bottom bone contacting head portion surface is anatomically contoured to match the contour of the rotated cut tibia segment.

4. The bone plate of claim 1 in which the elongated shaft opposing sides have spaced curved notches for bending the head portion relative to the elongated shaft to vary said angle between the centerline of the head portion and the centerline of the elongated shaft during a TPLO procedure.

5. The bone plate of claim 4 which the spaced curved notches are disposed between adjacent shaft screw holes in the elongated shaft.

6. The bone plate of claim 1 in which the elongated shaft bottom bone contacting shaft surface includes spaced transverse grooves to reduce contact between the elongated shaft bottom surface and the lower portion of the tibia.

7. The bone plate of claim 1 in which the screw holes in the elongated shaft and/or head portion include a central opening, a plurality of bores spaced around said central opening and intersection surfaces formed from a common intersection of the central opening and adjacent bores.

8. The bone plate of claim 7, in which one or more screw holes further include a countersink above said intersection surfaces for a non-locking screw.

9. The bone plate of claim 1 in which the bone plate is made of a titanium alloy.

10. The bone plate of claim 1 further including one or more k-wire holes.

11. The bone plate of claim 1 in which the shaft has a beveled distal end.

12. The bone plate of claim 1 in which the head portion has a beveled proximal end.

13. The bone plate of claim 1 further including a contoured registration mark on the top surface of the plate proximate the transition to assist a surgeon in placing the bone plate on the rotated cut segment of the upper tibia.

14. The bone plate of claim 1 configured as a drill guide plate and further including drill guide ports extending upwards from the shaft top surface and head portion top surface and oriented to overlie the screw holes in a bone plate.

15. A set of different size bone plates dimensioned for securing a rotated cut segment of an upper tibia to a lower portion of the tibia as part of a tibial leveling osteotomy procedure for an animal, each bone plate comprising:
   an elongated shaft with a top surface and bottom bone contacting shaft surface between opposing side of the bone plate;
   shaft screw holes in the elongated shaft extending from the top surface to the bottom bone contacting shaft surface for securing the elongated shaft to the lower portion of the tibia;
   a head portion extending from the elongated shaft with a top surface and a bottom bone contacting head portion surface between opposing sidewalls;
   head portion screw holes in the head portion extending from the top surface to the bottom bone contacting head portion surface thereof for securing the head portion to the rotated cut segment of the upper tibia;
   a transition between the elongated shaft and head portion including opposing concave sidewalls;
   the elongated shaft having a centerline located centrally between opposing sides of the shaft and the head portion having a centerline located centrally between the opposing sidewalls of the head portion angled with respect to the centerline of the elongated shaft at an angle of 25°-30° to dispose the elongated shaft collinear or approximately collinear with respect to the lower portion of the tibia and to fit the head portion to the rotated cut segment of the upper tibia;
   the head portion having a crescent shape and including two outer head portion screw holes, a first outer lobe about one outer head portion screw hole and a second outer lobe about the other outer head portion screw hole, a dip between the two outer lobes at the centerline of head portion, and a third head portion screw hole between the two outer head portion screw holes;
   the centerline of the shaft bisecting all the shaft screw holes;
   the centerline of the head portion intersecting the third head portion screw hole; and
   said angle between the centerline of the elongated shaft and the centerline of the head portion being different for different size bone plates in the set.

16. The bone plate set of claim 15 in which each shaft portion lies in a first plane and each head portion is bent upwardly and lies in a second plane angled with respect to the first plane and the head portion has a twist bend.

17. The bone plate set of claim 15 in which each head portion bottom bone contacting head portion surface is anatomically contoured to match the contour of the rotated cut tibia segment.

18. The bone plate set of claim 15 in which each elongated shaft opposing sides have spaced curved notches for bending the head portion relative to the elongated shaft to vary said angle between the centerline of the head portion and the centerline of the elongated shaft during a TPLO procedure.

19. The bone plate set of claim 18 in which the spaced curved notches are disposed between adjacent screw holes and the elongated shaft.

20. The bone plate set of claim 15 further including one or more k-wire holes.

21. The bone plate set of claim 15 in which the shaft has a beveled distal end.

22. The bone plate set of claim 15, in which the head portion has a beveled proximal end.

23. The bone plate set of claim 15 further including a contoured registration mark on the top surface of the plate proximate the transition to assist a surgeon in placing the bone plate on the rotated cut segment of the upper tibia.

24. The bone plate set of claim 15 in which a bone plate is configured as a drill guide plate and further including drill guide ports extending upwards from the shaft top surface and head portion top surface and oriented to overlie screw holes in a bone plate.

25. The bone plate of claim 1 in which the centerline of the shaft intersects an outer head portion screw hole.

26. The bone plate of claim 15 in which the centerline of the shaft intersects an outer head portion screw hole.

* * * * *